United States Patent
Lee et al.

(10) Patent No.: US 10,758,401 B2
(45) Date of Patent: Sep. 1, 2020

(54) EXCRETA DISPOSAL DEVICE INCLUDING MALE MODULE HAVING OPENING FACING HUMAN BODY

(71) Applicant: CURACO, INC., Seongnam-si, Gyeonggi-do (KR)

(72) Inventors: Hoonsang Lee, Seoul (KR); Sung Pil Choi, Seoul (KR); Dong Hoon Lee, Gwangju-si (KR); Byung Woong Lee, Suwon-si (KR)

(73) Assignee: CURACO, INC., Seongnam-si, Gyeonggi-do (KR)

( * ) Notice: Subject to any disclaimer, the term of this patent is extended or adjusted under 35 U.S.C. 154(b) by 556 days.

(21) Appl. No.: 15/531,761

(22) PCT Filed: Jul. 27, 2015

(86) PCT No.: PCT/KR2015/007819
§ 371 (c)(1),
(2) Date: May 31, 2017

(87) PCT Pub. No.: WO2016/088975
PCT Pub. Date: Jun. 9, 2016

(65) Prior Publication Data
US 2017/0266032 A1    Sep. 21, 2017

(30) Foreign Application Priority Data

Dec. 1, 2014  (KR) .......................... 10-2014-0169877
Dec. 1, 2014  (KR) .......................... 10-2014-0169885

(51) Int. Cl.
*A61F 5/453*   (2006.01)
*A61G 7/02*    (2006.01)
(Continued)

(52) U.S. Cl.
CPC ................ *A61F 5/453* (2013.01); *A61G 7/02* (2013.01); *A61G 9/00* (2013.01); *A61G 9/02* (2013.01); *A61F 5/451* (2013.01); *A61G 9/006* (2013.01)

(58) Field of Classification Search
CPC combination set(s) only.
See application file for complete search history.

(56) References Cited

U.S. PATENT DOCUMENTS 3,626,941 A * 12/1971  Webb ........................ A47K 7/08
                                                              604/291
4,588,397 A *  5/1986  Giacalone ............... A61F 5/453
                                                              604/349
(Continued)

FOREIGN PATENT DOCUMENTS

JP    2004267400 A    9/2004
KR    20120091682 A   8/2012
(Continued)

OTHER PUBLICATIONS

Int'l Search Report dated Nov. 24, 2015 in Int'l Application No. PCT/KR2015/007819.

*Primary Examiner* — Tatyana Zalukaeva
*Assistant Examiner* — Guy K Townsend
(74) *Attorney, Agent, or Firm* — Panitch Schwarze Belisario & Nadel LLP

(57) ABSTRACT

An excreta disposal device is provided, which includes a main body formed with a first disposal space opened in a hip direction of a human body to receive excreta discharged from the human body, and has a storage space formed therein. A male module, in which a second disposal space configured to receive urine discharged from the human body, is formed inside, and an opening unit opened to face the human body of the user is formed on one side of the second disposal space. The second disposal space is formed to be (Continued)

capable of inserting at least a part of male genitalia and is provided in the main body. A suction port is provided in the storage space and communicates with at least one of the first disposal space and the second disposal space to discharge excreta to the outside of the main body.

16 Claims, 15 Drawing Sheets

(51) Int. Cl.
*A61G 9/02* (2006.01)
*A61G 9/00* (2006.01)
*A61F 5/451* (2006.01)

(56) References Cited

U.S. PATENT DOCUMENTS

| | | | | |
|---|---|---|---|---|
| 4,759,753 A * | 7/1988 | Schneider | ............... | A61F 5/453 604/352 |
| 4,791,686 A * | 12/1988 | Taniguchi | ............... | A61G 9/00 4/448 |
| 4,994,051 A * | 2/1991 | Walsh | ............... | A61F 5/453 604/349 |
| 5,066,711 A * | 11/1991 | Colon | ............... | A61F 13/15 524/556 |
| 5,342,583 A * | 8/1994 | Son | ............... | A61F 5/451 422/107 |
| 5,423,785 A * | 6/1995 | Hart | ............... | A61F 5/453 604/317 |
| 5,495,858 A * | 3/1996 | Steer | ............... | A61F 5/448 128/885 |
| 5,618,277 A * | 4/1997 | Goulter | ............... | A61F 5/4405 604/349 |
| 5,681,297 A * | 10/1997 | Hashimoto | ............... | A61F 5/451 119/164 |
| 5,809,586 A * | 9/1998 | Kitamura | ............... | A61H 35/00 4/443 |
| 6,110,159 A * | 8/2000 | Tsujita | ............... | A61F 5/451 4/420.2 |
| 6,238,378 B1 * | 5/2001 | Perez | ............... | A61F 5/4404 604/317 |
| 6,351,858 B1 * | 3/2002 | Toia | ............... | A61G 9/00 220/4.01 |
| 6,585,709 B2 * | 7/2003 | Maimets | ............... | A61F 5/451 604/326 |
| 6,651,267 B1 * | 11/2003 | Utz | ............... | A61G 7/02 4/443 |
| 8,394,073 B1 * | 3/2013 | Williams | ............... | A61F 5/453 604/319 |
| 2003/0204176 A1 * | 10/2003 | Besoyan | ............... | A61F 5/4408 604/353 |
| 2007/0032765 A1 * | 2/2007 | Honda | ............... | A61F 5/451 604/347 |
| 2011/0022011 A1 * | 1/2011 | Edward | ............... | A61M 3/027 604/319 |
| 2016/0136338 A1 * | 5/2016 | Lee | ............... | A47K 3/26 604/319 |
| 2017/0266032 A1 * | 9/2017 | Lee | ............... | A61G 7/02 |
| 2018/0028386 A1 * | 2/2018 | Lee | ............... | A47K 10/48 |
| 2018/0042801 A1 * | 2/2018 | Lee | ............... | A47K 10/48 |

FOREIGN PATENT DOCUMENTS

| | | | | |
|---|---|---|---|---|
| KR | 10117921 B1 * | 9/2012 | ............ | A61F 5/453 |
| KR | 101179217 B1 * | 9/2012 | ............ | A61F 5/453 |
| KR | 101179217 B1 | 9/2012 | | |
| KR | 101299185 B1 | 8/2013 | | |

* cited by examiner

EXCRETA DISPOSAL DEVICE INCLUDING MALE MODULE HAVING OPENING FACING HUMAN BODY

CROSS-REFERENCE TO RELATED APPLICATION

This application is a section 371 of International Application No. PCT/KR2015/007819, filed Jul. 27, 2015, which was published in the Korean language on Jun. 9, 2016, under International Publication No. WO 2016/088975 A1, and the disclosure of which is incorporated herein by reference.

TECHNICAL FIELD

The present invention relates to an excreta disposal device which automatically disposes excreta discharged from a human body, and more particularly, to an excreta disposal device which includes a male module corresponding to a male body shape, and an opening unit of the male module is formed so as to face a human body.

BACKGROUND ART

In general, since people with difficulty moving disabilities or lower body based volunteers, such as patients and elderly, are not capable of handling their excreta, there was inconvenience that unless parents or carers are always present in the surroundings.

Therefore, in order to solve such inconvenience, excreta disposal units for recovering excreta by directly coming into contact with human body are being researched and developed. Such excreta disposal units are designed to receive the excreta of a user, and suck and discharge it to the outside of the disposal unit. Even if the guardian and carer are not resident around the user, the excreta disposal units automatically disposal the excreta.

However, the conventional excreta disposal units that have been developed up to now often concentrate only on the excreta disposal function, and are designed without considering the user's body. Thus, there is a problem that usability is very poor. Generally, the hip or the periphery of the genitals, from which the excreta is excreted, have a structure in which the bending is severe and the excreta disposal unit is hard to be adhered, and thus, in many cases, the excreta frequently leaks between the human body and the excreta disposal unit.

Also, users who use excreta disposal units such as patients and elderly often live in a state of lying on the bed, and there are many situations in which they do not change their own posture. If such a condition lasts for a long period of time, bedsores and the like will occur, so that there is a need to change the posture periodically. However, with the excreta disposal unit worn, there was a cumbersome task of removing the excreta disposal units since it is not possible to change their posture.

Furthermore, because the shape of the human body is formed very differently depending on sex, the structure needs to be different depending on sex, but in the past, since there have been no research and development on the excreta disposal units specialized for each sex, there has been inconvenience.

Therefore, a method for solving such a problem is required.

DISCLOSURE

Technical Problem

The present invention was devised to solve the conventional problems described above, and an object of the present invention is to provide an excreta disposal device which can prevent leakage of excreta and improve fitting feeling, while wearing by a user.

Another object of the present invention is to provide an excreta disposal device which cannot be restricted in behavior even when worn.

Still another object of the present invention is to provide an excreta disposal device capable of providing a specialized structure according to the shape of a male body.

The problems of the present invention are not limited to the above-mentioned problems, and another problem which is not mentioned can be clearly understood by those skilled in the art from the description below.

Technical Solution

To achieve the aforementioned object, an excreta disposal device formed with an opening unit facing a human body of the present invention includes: a main body which is formed with a first disposal space opened in a hip direction of a human body to receive excreta discharged from the human body, and has a storage space formed therein; a male module in which a second disposal space configured to receive urine discharged from the human body is formed inside, an opening unit opened to face the human body of the user is formed on one side of the second disposal space and the second disposal space and formed to be capable of inserting at least a part of male genitalia and provided in the main body; and a suction port which is provided in the storage space and communicates with at least one of the first disposal space and the second disposal space to discharge excreta to the outside of the main body.

Further, at least a part of an inner surface of the male module may be formed in the form of a downward inclined curve.

Also, at least a part of the male module may be formed to be vertically rotatable.

Further, the male module may include a coupling unit coupled to the body; and an insertion part connected to the coupling unit and having the second disposal space formed therein.

Also, the genital insertion unit may be connected to the coupling unit to be rotatable up and down.

Further, the genital insertion unit may include a connecting unit connected to the coupling unit; and an insertion part which is provided in front of the connecting unit and has the opening unit formed therein.

Also, the insertion part may be detachably formed in the connecting unit.

Further, the insertion part may be linearly movable in the connecting unit and may be formed to be able to adjust the length of the genital insertion unit.

Also, an extension unit formed to have a predetermined length and inserted inside the connecting unit is formed at a rear end of the insertion part, and the connecting unit may be provided with a fixing member configured to fix the extension unit.

Further, a plurality of catching grooves are formed at the rear end of the insertion part along the length direction of the insertion part, and the connecting unit may be provided with a catching member selectively coupled to any one of the plurality of catching grooves.

Also, a screw thread is formed around the rear end of the insertion part, and the connecting unit may be provided with a screw thread engaged with a screw thread of the insertion part, and a rotating member configured to move the insertion part back and forth in accordance with rotation.

Further, the coupling unit may be detachably formed in the main body.

Also, the coupling unit may be provided with a coupling unit which projects to a predetermined length and is inserted into the main body.

Further, a coupling depth between the main body and the coupling unit is adjustable.

Also, the excreta disposal device may further include at least one or more coupling adjusting members which are provided so as to surround a part of the whole length of the coupling unit, and adjusts the depth of the coupling between the main body and the coupling unit by increase and decrease of the number.

Further, the male module may further include a genitals fixing unit which is exposed to the second disposal space and crimps and fixes the male unit inserted into the second disposal space.

Also, the genitals fixing unit may be formed so as to be able to adjust the length exposed to the second disposal space.

Further, the genitals fixing unit may include an adjustment member in which one side thereof is exposed to the second disposal space and the other side thereof is exposed to the outside of the male module so that the length exposed to the second disposal space can be adjusted in accordance with external manipulation; and a crimping member provided on one side of the adjustment member to crimp and fix the male genitalia.

Also, at least a part of the male module may include a plurality of open regions in which a part of the periphery is opened so that the second disposal space is exposed to the outside, and a non-open region provided between the plurality of open regions.

Further, the excreta disposal device may further include a skin formed to cover the periphery of the male module to shield the open region.

Advantageous Effects

The excreta disposal device including the male module having the opening unit facing the human body of the present invention for solving the above problem has the following effects.

First, since the device includes a body corresponding to the hip and a male module corresponding to the male genitalia, there are advantages that the device provides a comfortable fit, and even in the worn state, the user does not have restrictions on the behavior, and the posture can be freely changed.

Second, since the device provides a male module specialized in the structure of the body of male, there is an advantage that it is possible to stably fix the male genitals with high degree of freedom of movement to smoothly treat the excreta.

Third, since the opening unit is downwardly oriented so as to correspond to the genital orientation of a male, it is possible for the user to position the genitalia naturally without feeling foreign matter when wearing, and even in the case where the device is worn by other users, it is easy to wear the device.

Fourth, since the male module may be formed to be rotatable so as to correspond to each other based on the position and posture of male genitals, there are advantages that, when the user wears the male module, the genitals can be positioned naturally without feeling foreign matter, it can be easily worn even when the device is worn by other users The effects of the present invention are not limited to the effects mentioned above, and another effect which is not mentioned can be clearly understood by those skilled in the art.

DESCRIPTION OF DRAWINGS

The detailed description of the preferred embodiments of the present application to be described below, and the aforementioned summary will be able to better understand when read in conjunction with the accompanying drawings. The preferred embodiments are illustrated in the drawings for the purpose of illustrating the present invention. However, it should be understood that the present application is not limited to the illustrated precise arrangements and means.

BEST MODE

Figure 1:
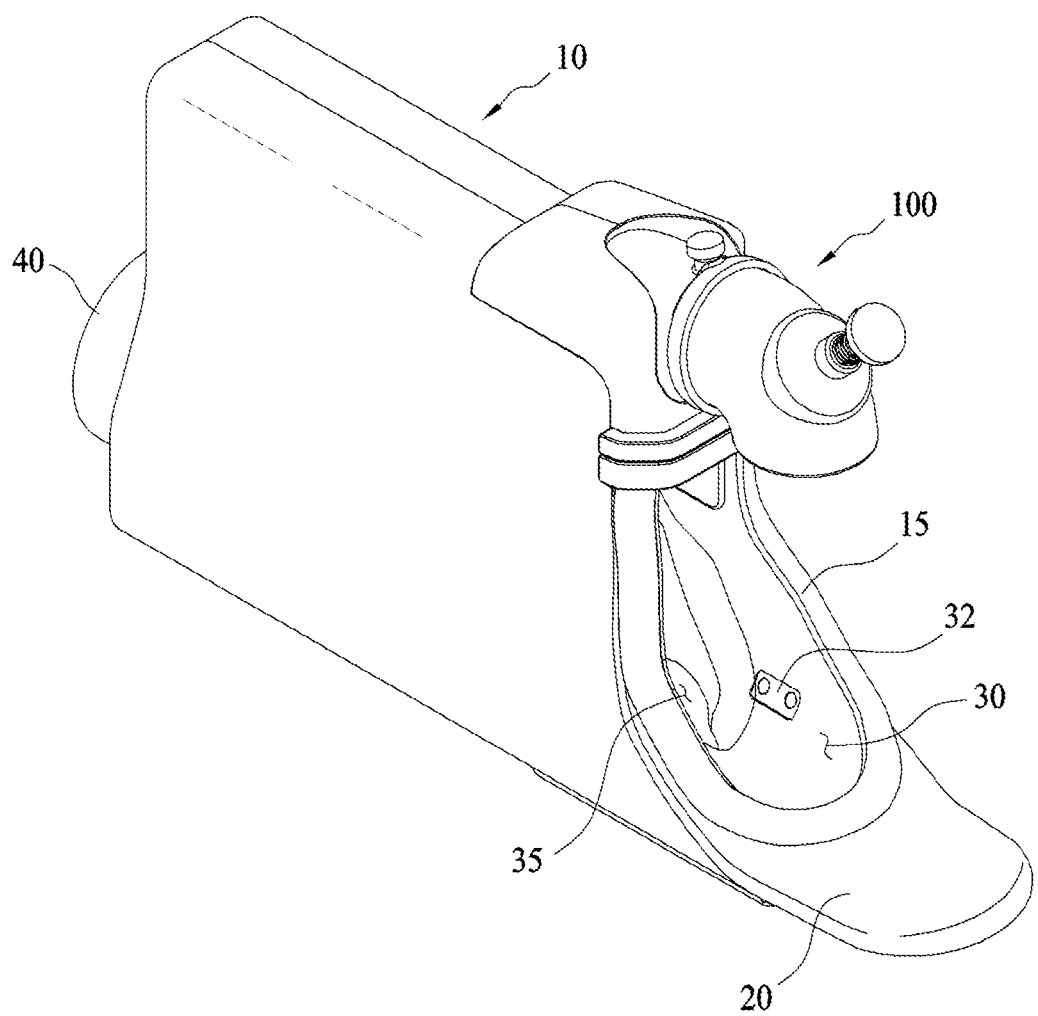
FIG. 1 is a perspective view illustrating the overall appearance of an excreta disposal device according to a first embodiment of the present invention.

Hereinafter, embodiments of the invention will be described in detail with reference to the accompanying drawings. The drawings attached hereto are to help explain exemplary embodiments of the invention, and the present invention is not limited to the drawings and embodiments.

Preferred embodiments of the present invention will now be described with reference to the accompanying drawings. In describing the embodiment, the same name and the same reference numeral will be used for the same configuration, and an additional explanation will be omitted.

Figure 2:
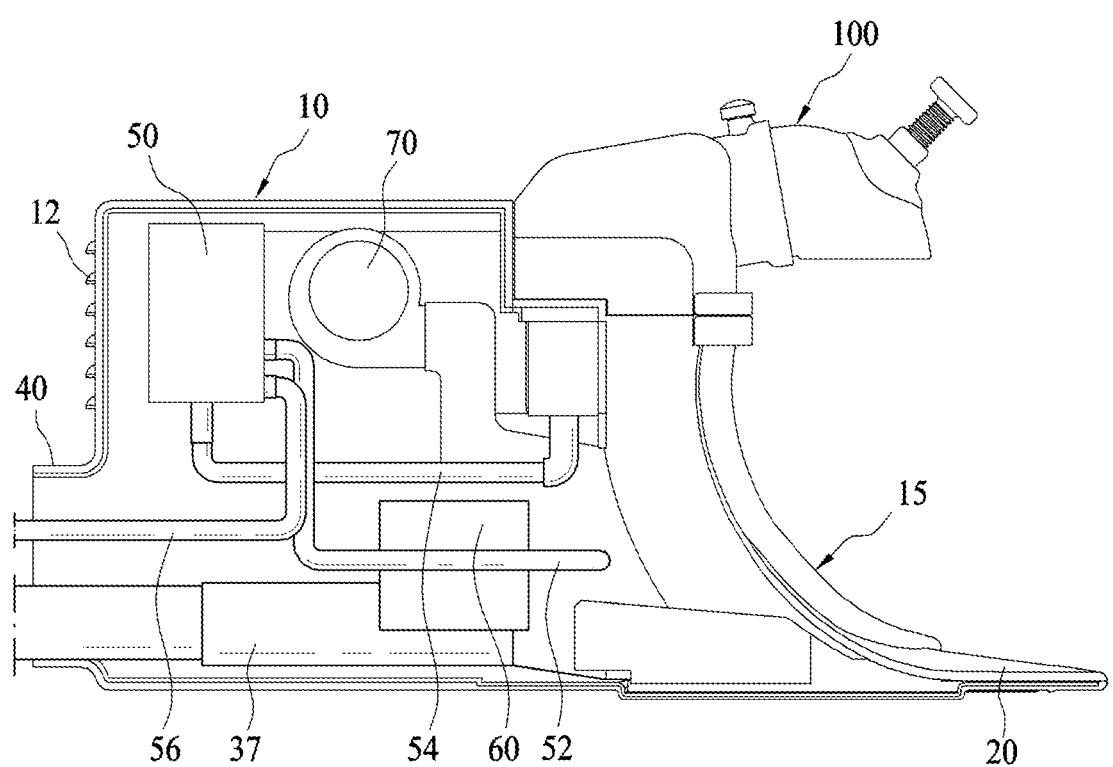
FIG. 2 is a perspective view illustrating the internal structure of the body in the excreta disposal device according to the first embodiment of the present invention.

FIG. 1 is a perspective view illustrating the overall appearance of an excreta disposal device according to a first embodiment of the present invention, and FIG. 2 is a perspective view illustrating an internal structure of a main body 10 in the excreta disposal device according to the first embodiment of the present invention.

As illustrated in FIGS. 1 and 2, the excreta disposal device according to the first embodiment of the present invention includes a main body 10, a male module 100, and a suction port 35.

The main body 10 is formed with a first disposal space 30 opened in a hip direction of the human body to receive excreta discharged from the human body, and a storage space is formed therein.

In the present embodiment, the main body 10 has a width corresponding to the space between the user's legs and a height corresponding to the user's inguinal part.

On the other hand, for the sake of convenience in the following explanation, the open direction side of the first disposal space 30 is defined as a front side, and the opposite direction thereof is defined as a rear side. Further, the direction in which the male module 100 is provided is defined as an upper part, and the opposite direction thereof is defined as a lower part.

That is, in a state where the legs are stretched on both sides of the main body 10, the user can stably mount the excreta disposal device 1 by placing the hip on the side of the first disposal space 30.

In this embodiment, a fitting unit 15 with a curve corresponding to the inguinal part and the hip of the user is provided around the first disposal space 30 to increase the fitting. A support unit 20 for supporting the hip of the user is provided in front of the lower unit of the first disposal space 30, and the support unit 20 is connected with the seating unit 15 to have a natural curve to be able to comfortably support the user's body.

In addition, a sensing sensor 32 for sensing excreta in the first disposal space 30 is provided inside the first disposal space 30. When the sensing sensor 32 detects the excreta in the first disposal space 30, another suction device can suck the excreta in the first disposal space 30 through the suction port 35.

The suction port 35 is a component which is formed inside the excreta floating tube 37 provided in the storage space of the main body 10, and communicates with the first disposal space 30 to discharge the excreta in the space 30 to the outside of the main body 10. In this way, excreta discharged to the outside of the main body 10 may be stored in a predetermined storage area, or may be discharged without being stored.

Particularly, in the present embodiment, a through unit 40 is formed behind the main body 10 so that an external connector connected to another suction device can be drawn into the inside of the storage space.

On the other hand, in the case of this embodiment, the suction port 35 is configured to communicate with the first disposal space 30, but unlike this, the suction port 35, of course, can also be directly connected to the second disposal space S (see FIG. 9) of the male module 100 to be described later. This will be described later.

Further, various components may be provided inside the storage space of the main body 10. In the present embodiment, a flow channel switching unit 50 and an air blowing unit 70 are provided in the storage space, including the excreta floating tube 37 having the above-mentioned suction port 35.

The flow channel switching unit 50 is a component which is connected to a cleaning water flowing tube 56 flowing in through the through unit 40 and receives cleaning water from the outside, and can supply the cleaning water to at least one side of the first disposal space 30 and the second disposal space to be described later (S, see FIG. 9) through the solenoid valve or the like.

Specifically, in the case of the present embodiment, the cleaning water stored in the flow channel switching unit 50 can be supplied to the first disposal space 30 side via the first supply tube 52, and can be supplied to the second disposal space (S, see FIG. 9) side through the second supply tube 54. Further, the cleaning water flowed to the first disposal space 30 side is injected into the first disposal space 30 by a first spraying unit 60, and the cleaning water flowed to the second disposal space (S, see FIG. 9) side is injected into the second disposal space (S, see FIG. 9) via an injection nozzle 135, which will be described later.

The air blowing unit 70 is a component that blows drying air to the first disposal space 30, and generates the drying air with a blower fan or the like to blow the drying air to the first disposal space 30 side through a dying air injection port exposed to the first disposal space 30. Further, a heater may be further provided for raising the temperature of the drying air.

In the present embodiment, an air inlet 12 is formed on the rear surface of the main body 10 to allow external air to flow to ventilate the inside of the storage space.

A configuration of the main body 10 as described above is a single embodiment, and the constituent elements provided in the storage space, of course, may be changed, adjusted, or modified in various ways.

Figure 3:
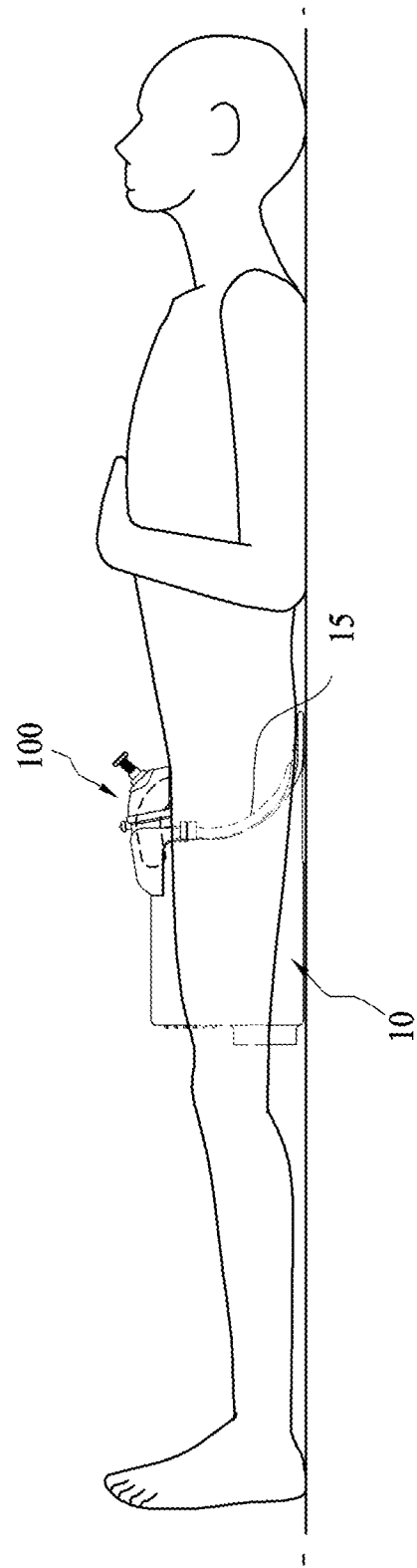
FIG. 3 is a side view illustrating a state in which a user wears the excreta disposal device according to the first embodiment of the present invention.

FIG. 3 is a side view illustrating a state in which a user wears the excreta disposal device according to the first embodiment of the present invention.

As illustrated in FIG. 3, in a state in which the user lies on a bed or the like, the user brings the seated unit 15 of the main body 10 into close contact with the groin unit and the hip, and stretches the legs to both sides of the main body 10. In such a state, it is possible to stably wear the excreta disposal device by inserting genitalia into the male module 100 provided on the upper part of the main body 10.

As described above, since the excreta disposal device according to the embodiment of the present invention is formed to correspond to the shape of the human body, it is not necessary for the user to forcibly change the posture according to the excreta disposal apparatus, and can maintain a natural posture.

Furthermore, even when the user changes the posture laterally, etc., the excreta disposal device can move along the body of the use without being detached, and even when the user behaves, the excreta disposal device does not interfere with the behavior in the state of being located between the legs.

Hereinafter, the male module 100 will be described in more detail.

Figure 4:
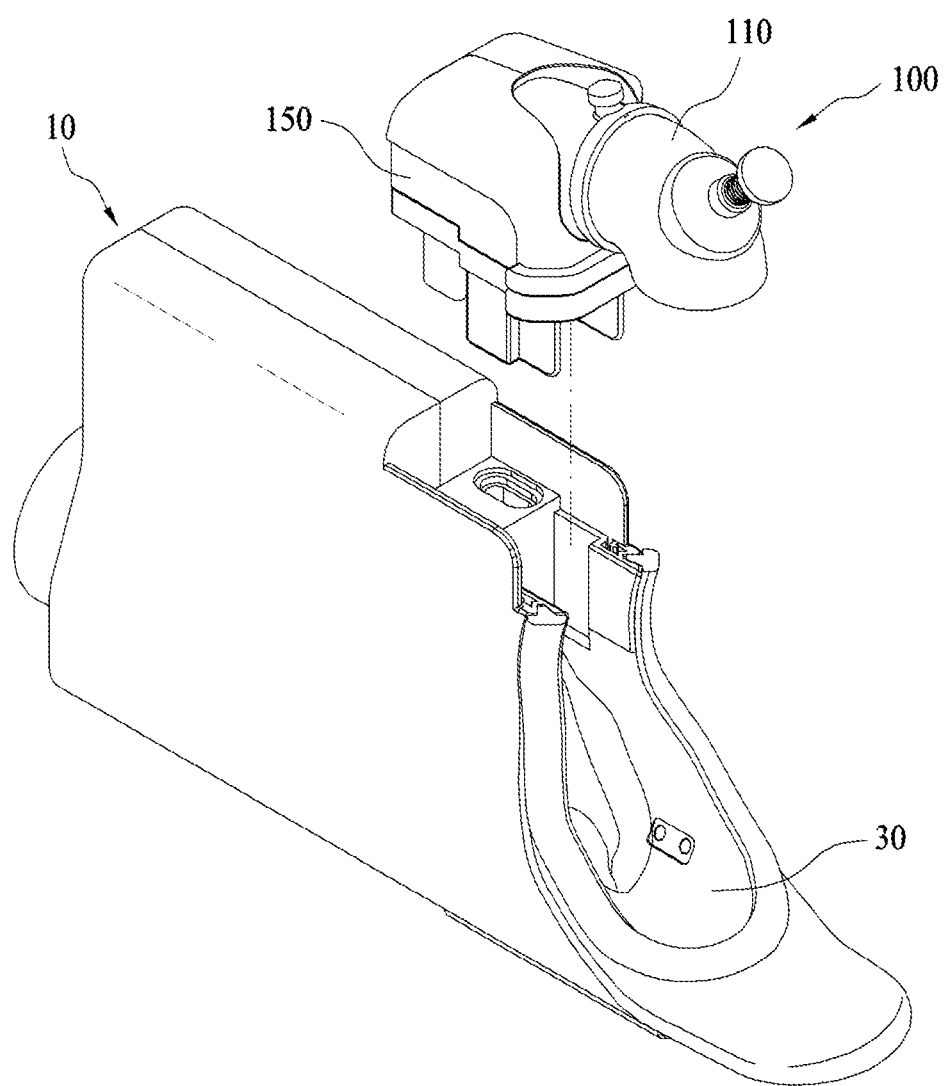
FIG. 4 is a side view illustrating the appearance of a male module in detail in the excreta disposal device according to the first embodiment of the present invention.
Figure 5:
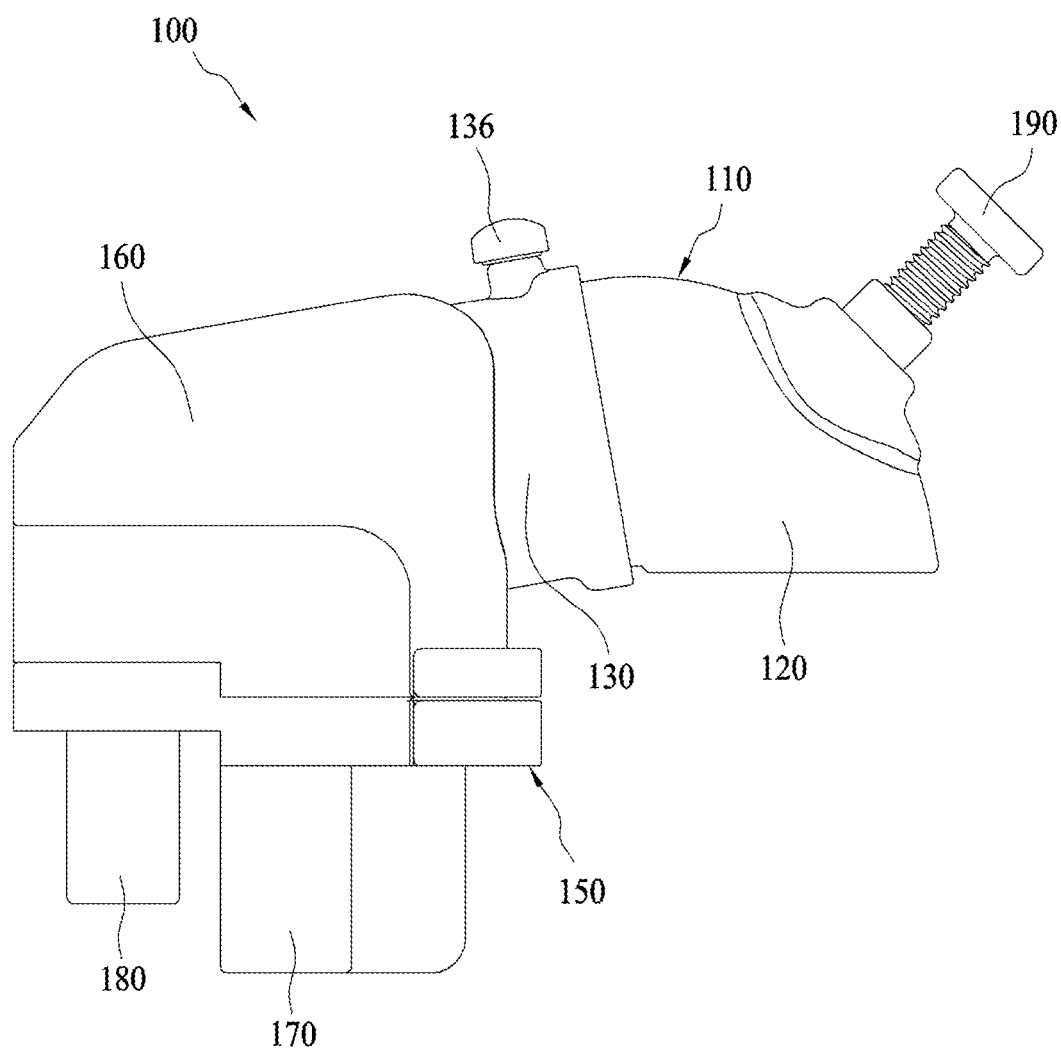
FIG. 5 is a perspective view illustrating the appearance of a male module from another direction in the excreta disposal device according to the first embodiment of the present invention.

FIG. 4 is a side view illustrating in detail the appearance of the male module 100 in the excreta disposal device according to the first embodiment of the present invention, and FIG. 5 is a perspective view illustrating a state of the male module 100 from another direction in the excreta disposal device according to the first embodiment of the present invention.

Figure 9:
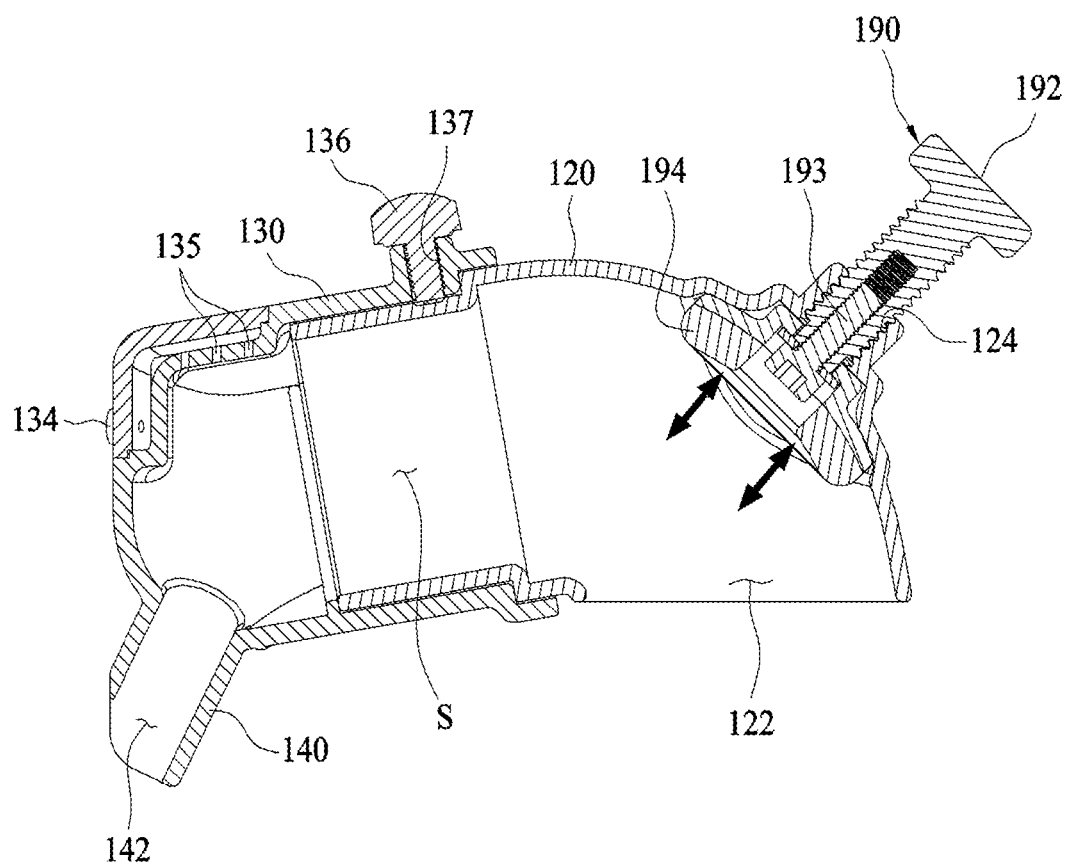
FIG. 9 is a cross-sectional view illustrating the internal structure of the genital insertion unit in the excreta disposal device according to the first embodiment of the present invention.

As illustrated in FIGS. 4 and 5, the male module 100 has a second disposal space (S, see FIG. 9) formed therein to receive urine discharged from the human body, and an opening unit 122 opened to face the human body of the user is formed on one side of the second disposal space (S, see FIG. 9). Thus, at least a part of the male genitalia can be inserted through the opening unit 122.

In this embodiment, the opening unit 122 has a form opened downward so as to face the user's genitalia.

Thus, in the male module 100 according to the present invention, since the opening unit 122 is formed so as to face the human body of the user, the user can naturally insert the genitalia into the inside of the male module 100, in the state of seating the main body (10, see FIG. 1), and it is possible to minimize constraints caused by changes in posture and changes in the position of genitals.

In the case of this embodiment, the male module 100 includes a coupling unit 150 coupled to the main body (10, see FIG. 1), and a genital insertion unit 150 connected to the coupling unit 110.

In addition, the genital insertion unit 110 includes a connecting unit 130 connected to the coupling unit 150, and an insertion part 120 provided in front of the connecting unit 130 and having the opening unit 122 formed therein.

The connection relations between the coupling unit 150 and the genital insertion unit 110, and between the coupling unit 130 and the insertion part 120 will be described later.

In this embodiment, the coupling unit 150 includes a coupling unit 170 to be coupled with the main body (10, see FIG. 1), and the coupling unit 170 protrudes to a predetermined length, and can be inserted into the main body (10, see FIG. 1).

Figure 10:
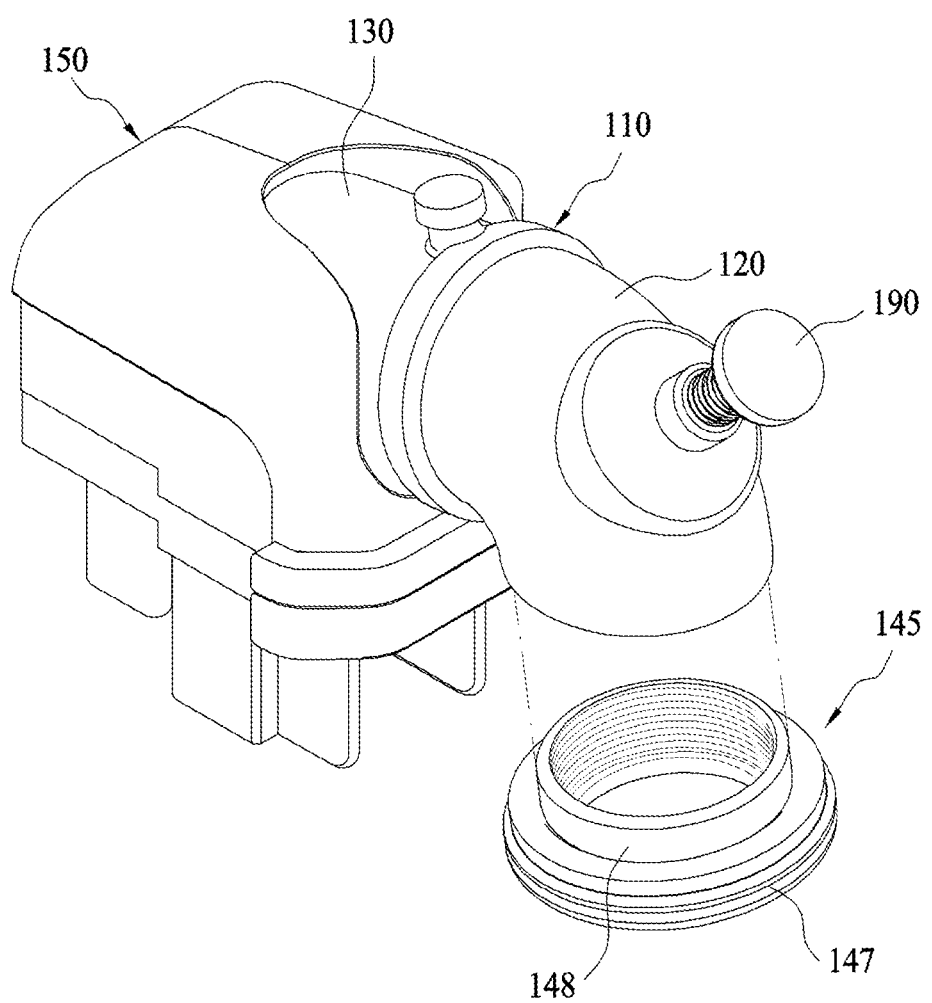
FIG. 10 is a perspective view illustrating a state in which a retractable adapter is coupled to a male module in the excreta disposal device according to the first embodiment of the present invention.

Meanwhile, in the case of this embodiment, an auxiliary coupling unit 180 is further provided at the rear of the coupling unit 170, the auxiliary coupling unit 180 also protrudes to a predetermined length, and is inserted into the main body (10, see FIG. 10). At this time, the auxiliary coupling unit 180 is connected to the above-mentioned second supply tube (54, see FIG. 2) so as to transmit cleaning water to the injection nozzle 135 side. That is, the auxiliary coupling unit 180 assists the coupling when the male module 100 is coupled, and forms the flow channel of the cleaning water.

Further, an excreta transmitting unit 140 is formed in the lower unit of the connecting unit 130 of the genital insertion unit 110 to allow the second disposal space (S, see FIG. 9) to communicate with the first disposal space (30, see FIG. 1). A communication flow channel 142 is formed inside the excreta transmitting unit 140 to transmit urine or cleaning water generated in the second disposal space (S, see FIG. 9) into the first disposal space (10, see FIG. 1) side.

In this way, in the present embodiment, the second disposal space (S, see FIG. 9) and the first disposal space (10, see FIG. 1) communicate with each other, but unlike this, it is a matter of course that the first and second disposal spaces may be formed separately from each other in some cases. In such a case, as described above, the suction port (35, see FIG. 1) branches and may be connected to each of the second disposal space (S, see FIG. 9) and the first disposal space (30, see FIG. 1), respectively.

Figure 6:
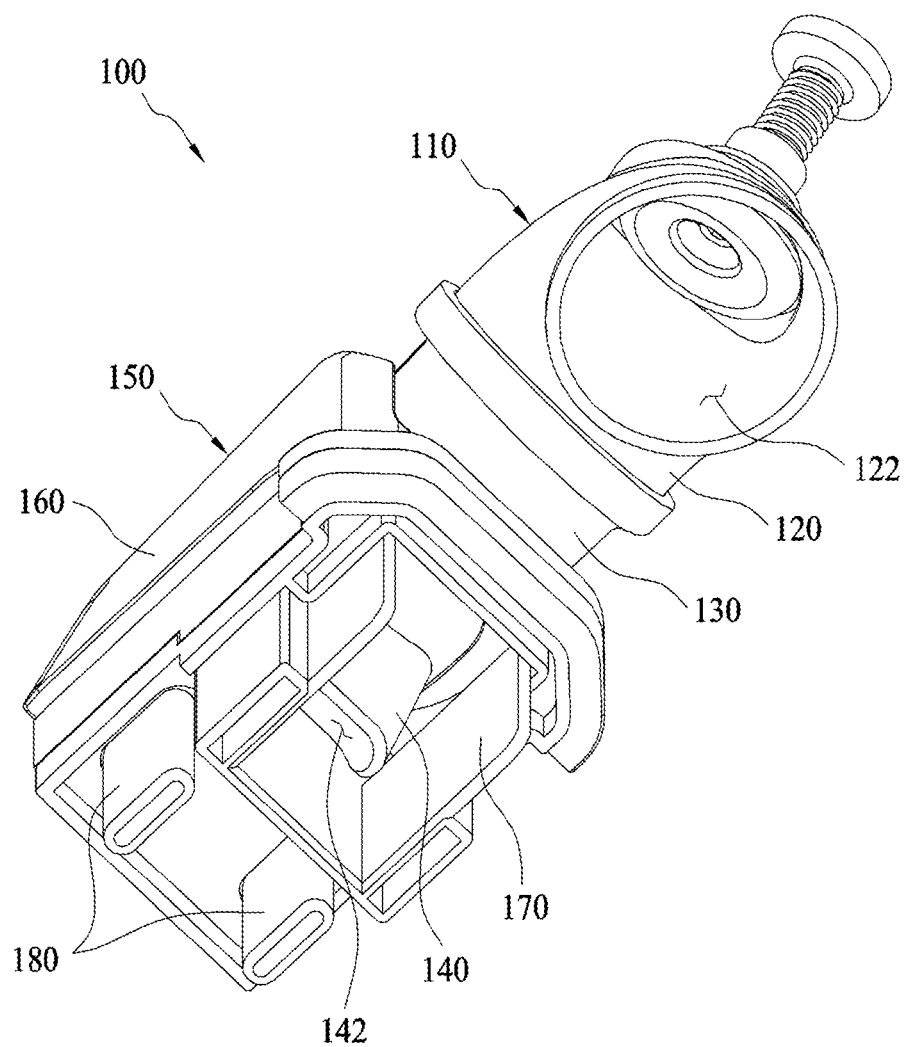
FIG. 6 is a perspective view illustrating a state in which a male module is coupled to a main body in the excreta disposal device according to the first embodiment of the present invention.

FIG. 6 is a perspective view illustrating a state in which the male module 100 is coupled to the main body 10 in the excreta disposal device according to the first embodiment of the present invention.

As illustrated in FIG. 6, in the present embodiment, the male module 100 is detachably formed on the main body 10. At this time, the coupling depth between the main body 10 and the coupling unit 150 can be adjusted, which will be described later.

Unlike the present embodiment, the male module 100 may, of course, be integrally formed on the main body 10.

Figure 7:
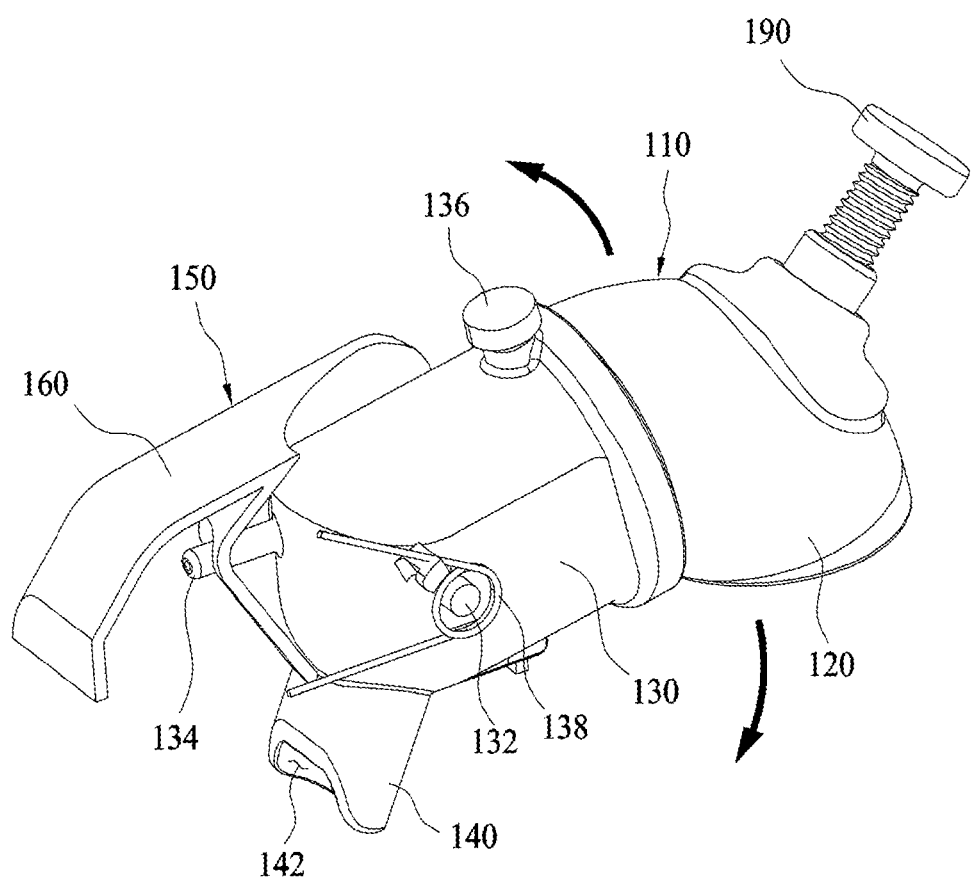
FIG. 7 is a perspective view illustrating the appearance in which the genital insertion unit of the male module gen is rotated in the up-down direction in the excreta disposal device according to the first embodiment of the present invention.

FIG. 7 is a perspective view illustrating an aspect in which the genitalia inserting unit 110 of the male module is rotated in the up-down direction in the excreta disposal device according to the first embodiment of the present invention.

As illustrated in FIG. 7, in the present embodiment, the insertion part 110 is connected to the coupling unit 150 to be rotatable in the up-down direction.

Specifically, shaft protrusions 132 are formed to protrude from both sides of the connecting unit 130 of the genital insertion unit 100 to form a rotating shaft, and the coupling unit 150 is formed with an insertion groove 132 into which the shaft protrusions 132 are inserted. Therefore, the genital insertion unit 100 can rotate in the vertical direction as a whole, and thus, even when the user changes the posture with the genitals inserted in the genital insertion unit 100, the genital insertion unit 100 is rotated so as to correspond to the movement of the genitals so that foreign body sensation does not occur.

Furthermore, there is an advantage that, even when the genitals are first inserted into the genital insertion unit 100, the genital insertion unit 100 can be properly rotated and easily worn.

On the other hand, in the case of this embodiment, a restoring member 138 for restoring the genital insertion unit 100 to the initial position is further provided. The restoring member 138 provides an elastic force to restore the genital insertion unit 100 to its initial position when rotated. In the present embodiment, the restoring member 138 is formed in the form of a torsion spring and is provided adjacent to the shaft protrusion 132.

Figure 8:
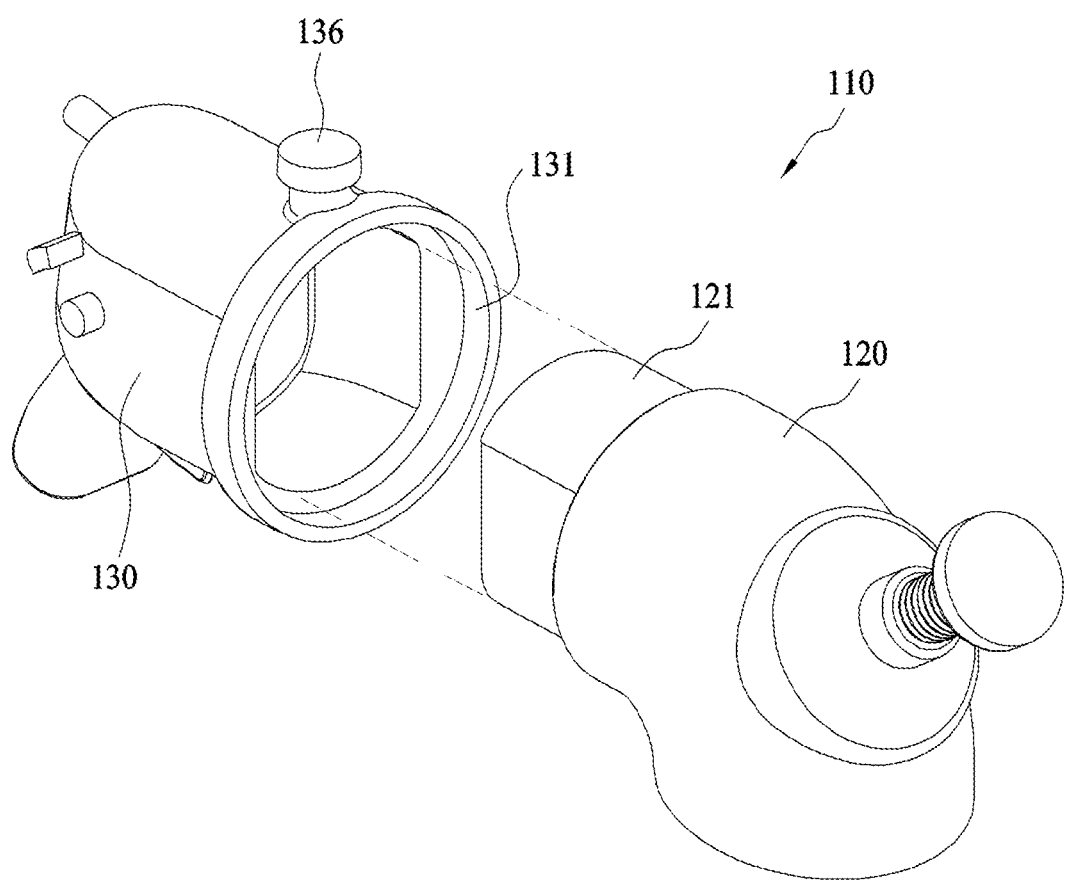
FIG. 8 is a perspective view illustrating a state in which the connecting unit and the insertion part of the genital insertion unit are separated from each other, in the excreta disposal device according to the first embodiment of the present invention.

FIG. 8 is a perspective view illustrating a state in which the coupling unit 130 and the insertion part 120 of the genital insertion unit 110 are separated from each other in the excreta disposal device according to the first embodiment of the present invention, and FIG. 9 is a cross-sectional view illustrating the internal structure of the genital insertion unit 110 in the excreta disposal device according to the first embodiment of the present invention.

As illustrated in FIGS. 8 and 9, in the present embodiment, the connecting unit 130 and the insertion part 120 of the genital insertion unit 110 are formed to be detachable from each other. Further, the insertion part 120 is formed to be linearly movable in the connecting unit 130, and is formed to be able to adjust the length of the genital insertion unit 110.

That is, the length of the genital insertion unit 110 can be adjusted so as to move the insertion part 120 back and forth from the connecting unit 130 to correspond to the body size of the user, and such length adjustment method can be provided in various ways.

In the case of this embodiment, an extension unit 121 which is formed to a predetermined length and is inserted into the connecting unit 130 is formed at the rear stage of the insertion part 120, and a fixing member 136 for fixing the extension unit 121 is provided in the connecting unit 130.

More specifically, in this embodiment, a first through hole 137 through which the fixing member 136 penetrates is formed in the connecting unit 130, and in the first through hole 137, a screw thread engaged with a screw thread formed around the fixing member is formed. Thus, the degree of pressurization of the extension unit can be adjusted, depending on the rotation of the fixing member.

However, the method by which the extension member 121 is fixed by the fixing member 136 is not limited thereto, and can be provided by various methods. For example, a plurality of through holes are sequentially formed in the extension unit 121, and the fixing member 136 may be fixed in a manner of being simultaneously inserted into one of the first through hole 137 and the through hole of the extension unit 121.

Further, when the insertion part 120 is completely separated from the connecting unit 130, the user's genitals is coupled to the connecting unit 130 in a state of being inserted into the insertion part 120 in advance, thereby making it possible to more easily insert the genitals into the male module. In such a case, when the user's genitals are inserted in the insertion part 120, the opening unit direction of the urethra is checked from the opposite side, the genitals is positioned at the correct position and can be coupled to the connecting unit 130, and thus, the device can be more easily used.

On the other hand, in the present embodiment, the male module includes a genitals fixing unit 190 which is exposed to the second disposal space S, and crimps and fixes the male unit inserted into the second disposal space S.

In particular, in the present embodiment, the genitals fixing unit 190 is formed on the side of the insertion part 120 and is formed so that the length exposed in the second disposal space S can be adjusted.

More specifically, the genitals fixing unit 190 includes a adjustment member 192 which has one side exposed to the second disposal space S and the other side exposed to the outside of the male module, and is formed so as to be adjustable in length exposed to the second disposal space S according to an external operation, and a crimping member 194 which is installed on one side of the adjustment member 192 for crimping and fixing the male genitalia.

At this time, a second through hole 124 is formed in the insertion part 120, and the second through hole 124 is formed with a screw thread formed around the adjustment member 192, and the crimping member 194 can move in accordance with the rotation of the adjustment member 192.

That is, even when the position and the size of the genitals change according to the situation, the above-mentioned genitals fixing unit 190 can fix the genitals so as not to depart from the fixed position, and at this time, in order to minimize pain of the user, at least a unit of the crimp member 194 could be formed to be stretchable.

Further, as described above, in the present embodiment, the connecting unit 130 is formed with an injection nozzle 135 for injecting the cleaning water. At this time, the cleaning water is supplied to the inflow tube 134 formed behind the connecting unit 130 via the second supply tube (54, see FIG. 2) and the auxiliary connecting unit 180, and can be injected through the injection nozzle 135.

On the other hand, as described above, the male module according to the present invention is formed such that the opening unit 122 is opposed to the human body, and at this time, at least part of the inner surface of the male module can be formed into a form of downward inclined curve. That is, since the inner surface of the male module is formed in the form of a downward inclined curve, it corresponds to the curvature of the genitals, which makes it possible to provide a more comfortable fit.

In the case of the present embodiment, the inner surface of the insertion part 120 was formed in the form of a downward inclined curve, but unlike this, it is a matter of course that the entire inner surface of the genital insertion unit 110 is may be formed in the form of a curve, or some other areas may be formed in the form of a curve.

FIG. 10 is a perspective view illustrating a state in which a retractable adapter 145 is coupled to a male module in the excreta disposal device according to the first embodiment of the present invention.

As illustrated in FIG. 10, in the case of the present embodiment, it is possible to further include an extension adapter 145 which is detachably provided around the opening unit of the male module and formed so that at least a region in contact with the human body has stretchability.

That is, the stretchable adapter 145 can further improve the user's fit and can prevent the genitals from being scratched around the opening unit when the user inserts genitals into the male module.

In this embodiment, the stretchable adapter 145 includes a fastening unit 148 formed in a shape corresponding to the opening unit of the male module and coupled to the opening unit, and a buffer unit 147 formed so as to enclose the side surface and the lower unit of the fastening unit 148 and formed of a material having elasticity.

Figure 11:
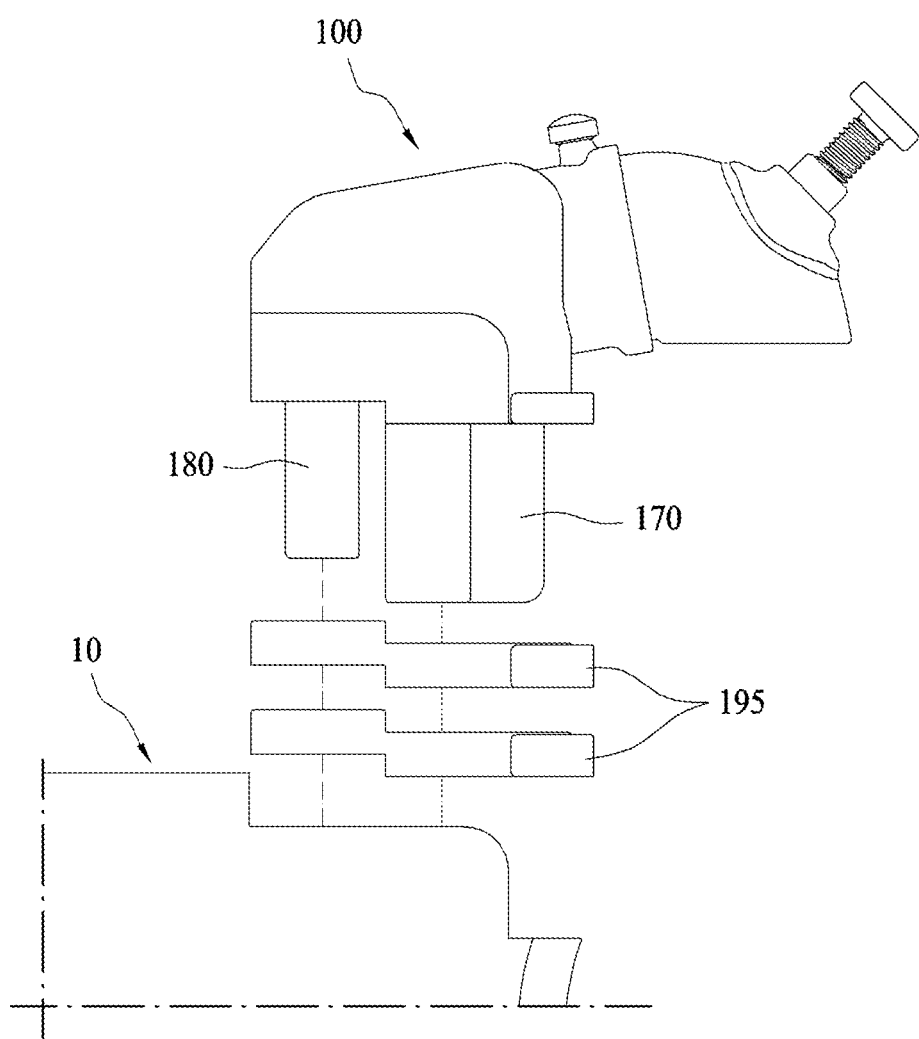
FIG. 11 is a side view illustrating a state in which a coupling adjusting member is provided between a male module and a main body in the excreta disposal device according to the first embodiment of the present invention.

FIG. 11 is a side view illustrating a state in which a coupling adjustment member 195 is provided between the male module 100 and the main body 10 in the excreta disposal device according to the first embodiment of the present invention.

As mentioned above, the male module 100 can be formed to adjust the depth of coupling with the main body 10, which can be provided in various ways.

In the case of this embodiment, the male module includes a coupling adjustment member 195 which is provided by one or more so as to surround a part of the entire length of the coupling unit 170, and adjusts the coupling depth of the coupling member 195 between the main body 10 and the coupling unit 170 by increase and decrease of the number.

That is, one or more coupling adjustment member 195 can be provided between the male module 100 and the main body 10, and serves to separate the coupling unit 170 so as not to be completely inserted into the main body 10.

At this time, a plurality of coupling adjustment member 195 may be provided, and the height of the male module 100 can be increased according to an increase in the number. Therefore, it is possible to use the coupling adjustment members 195 by adjusting the number, depending on the body size of the user.

In addition to the same method as in the present embodiment, various methods for adjusting the coupling depth of the male module 100 can be performed. For example, the coupling unit 170 and the auxiliary coupling unit 180 of the male module 100 may be inserted into the main body 10 in a stepwise sliding manner to adjust the coupling depth.

Figure 12:
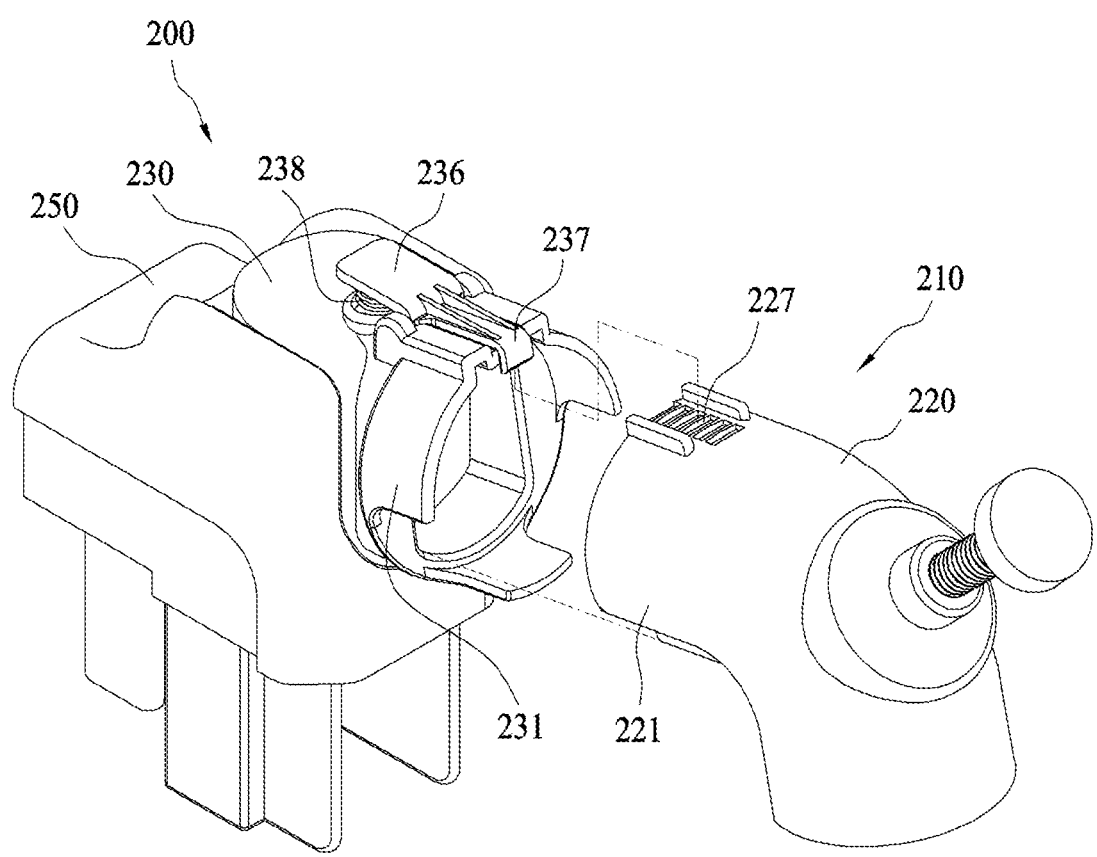
FIG. 12 is a perspective view illustrating a state in which the connecting unit and the insertion part of the genital insertion unit are separated from each other in the excreta disposal device according to a second embodiment of the present invention.

FIG. 12 is a perspective view illustrating a state in which the coupling unit 230 and the insertion part 220 of the genital insertion unit 210 are separated in the excreta disposal device according to the second embodiment of the present invention.

In the second embodiment of the invention illustrated in FIG. 12, all the components of the male module 200 are formed in the same way as in the first embodiment described above, but the coupling method of the connecting unit 230 and the insertion part 220 is differently formed.

Specifically, in the case of the present embodiment, a plurality of catching grooves 227 are formed along the length direction of the insertion part 210 at the rear stage of the insertion part 210, and the connecting unit 230 is provided with a catching member 237 selectively coupled to any of the plurality of catching groove 227.

That is, the length of the genital insertion unit 210 can be determined depending on the condition in which the catching member 237 is coupled to any one of the plurality of catching grooves 227.

In the present embodiment, the catching member 237 is provided in a hinge manner and presses the catching groove 227 by the elastic member 238, and in this case, in order to improve usability, a pressing unit 236 is formed behind the catching member 237 so that the user can operate the catching member 237.

Figure 13:
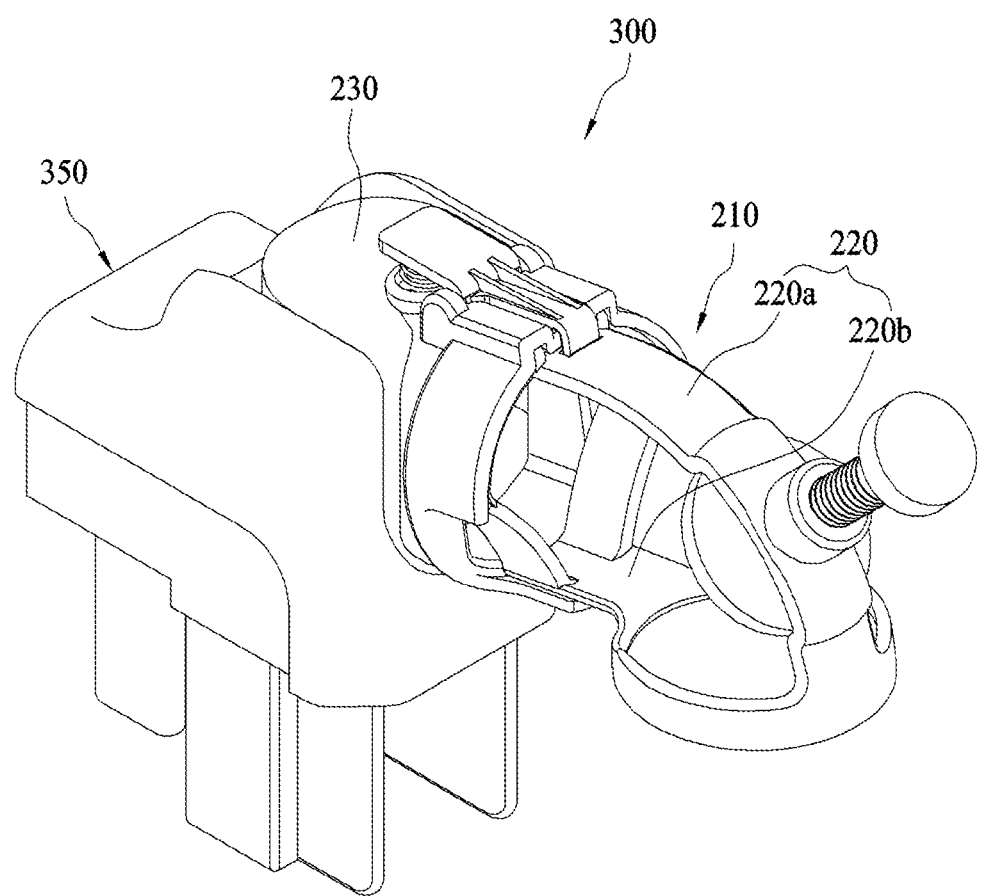
FIG. 13 is a perspective view illustrating a state of a genital insertion unit in the excreta disposal device according to the third embodiment of the present invention.

FIG. 13 is a perspective view illustrating a state of a genital insertion unit in the excreta disposal device according to the third embodiment of the present invention.

In the case of the third embodiment of the invention illustrated in FIG. 13, although all the components of the male module 200 are formed in the same way as in the first and second embodiments, the shape of the genital insertion unit 310 is slightly differently formed.

More specifically, in the present embodiment, at least a part of the male module 300 has a plurality of open regions in which a part of the periphery is opened so that the inner second disposal space is exposed to the outside, and a non-open region 320a provided between the plurality of open regions 320b. That is, in the case of this embodiment, at least a part of the male module 300 has a skeleton shape so that the second disposal space is exposed to the outside.

At this time, in the case of this embodiment, the open region 320b is assumed to be formed in the insertion part 320, but unlike this, it is a matter of course that the connecting unit 330 can also formed to have the open region 320b.

Although it is not illustrated, in such a case, a skin may be provided which surrounds the periphery of the male module 300 and shields the open region 320b. The skin is made of a flexible material such as rubber or cloth and can be placed on or separated from the male module 300, and has the advantage that the excreta disposal apparatus can be sanitarily used by exchanging and using the skin.

Figure 14:
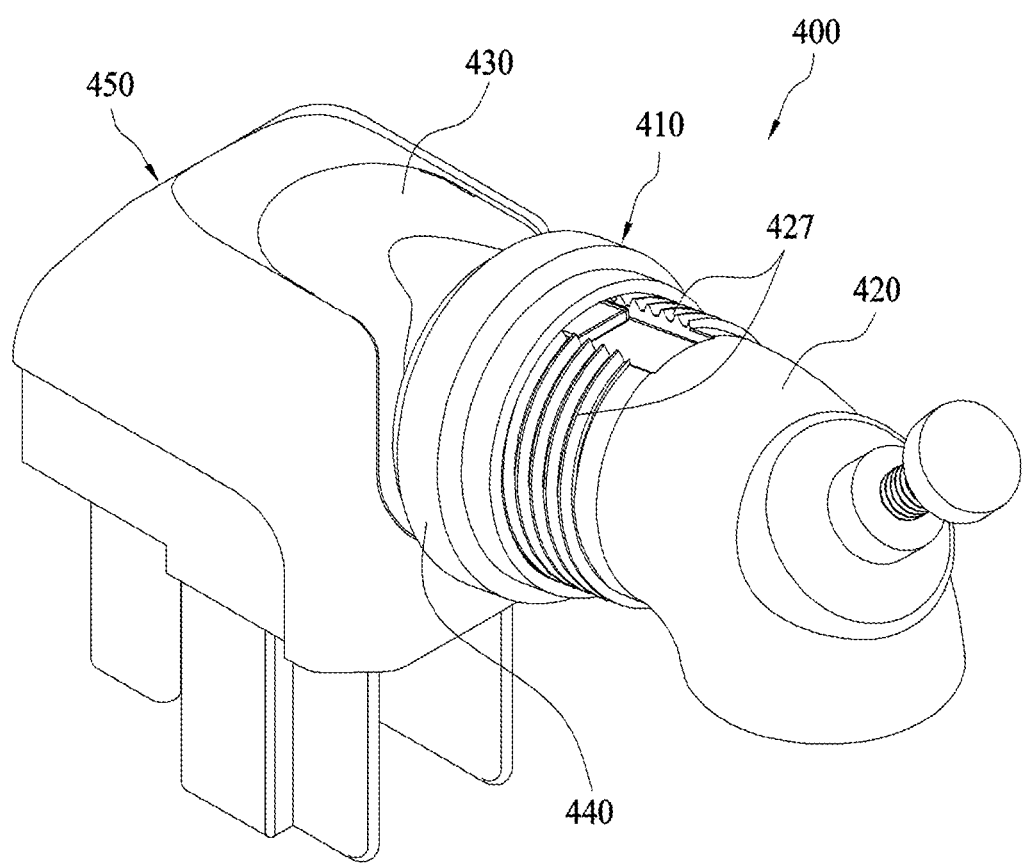
FIG. 14 is a perspective view illustrating a state of the genital insertion unit in the excreta disposal device according to a fourth embodiment of the present invention.

FIG. 14 is a perspective view illustrating the appearance of the genital insertion unit 410 in the excreta disposal device according to the fourth embodiment of the present invention.

In the case of the fourth embodiment of the present invention illustrated in FIG. 14, all the components of a male module 400 are formed in the same manner as in the above-described first embodiment, but the connecting method of the connecting unit 430 and the insertion part 420 are formed by another method.

Specifically, in the present embodiment, screw threads 427 are formed around the rear stage of the insertion part 420. A screw thread engaged with the screw thread 427 of the insertion part 420 is formed in the connecting unit 430, and a rotation member 440 that moves the insertion part 420 back and forth according to rotation is provided.

That is, in the case of this embodiment, the rotation member 440 is rotatably coupled to the front stage of the connecting unit 430, and in this state, the insertion part 420 is inserted into the rotation member 440. When rotating the rotation member 440, the insertion part 420 can slide in the front-rear direction by the screw threads 427 of the insertion part 420 and screw threads of the rotation member 440.

In this way, it is possible to check that the linear movement method of the insertion part 420 is variously provided.

Figure 15:
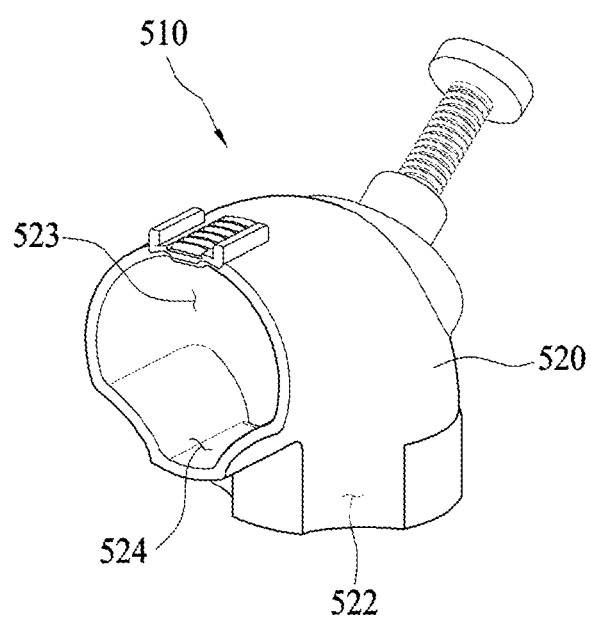
FIG. 15 is a perspective view illustrating a state of a genital insertion unit in the excreta disposal device according to a fifth embodiment of the present invention.

FIG. 15 is a perspective view illustrating the appearance of a genital insertion unit 510 in the excreta disposal device according to the fifth embodiment of the present invention.

In the case of the fifth embodiment of the invention illustrated in FIG. 15, the male module 510 is formed with a prostate protection groove 524 which is depressed in the region corresponding to the lower part of the male genitals.

That is, in the case of this embodiment, the lower part of the second disposal space 523 is formed in a depressed shape, thereby making it possible to prevent the prostate C part from being pressed by the male module 510 in a state in which the user inserts the genitals into the male module 510.

In the present embodiment, although the prostate protection groove 524 is assumed to be formed over the entire length of the lower part of the insertion part 520, the prostate protection groove 524 may be in the form of being formed only in a partial length of the lower part of the insertion part 520.

In addition, the prostate protection groove 524 may of course be formed on the connection side which is not illustrated.

While the preferred embodiments according to the present invention have been described, it will be obvious to those of ordinary skill in the art that the present invention can be embodied in other specific forms without depart from its spirit or categories, in addition to the previously described embodiments. Accordingly, the aforementioned embodiments should be considered as being illustrative rather than being limitive, and the present invention may be varied within the category of the appended claims and their equivalents, without being limited to the foregoing description, accordingly.

The invention claimed is:

1. A excreta disposal device comprising:
a main body which is formed with a first disposal space opened in a hip direction of a human body to receive excreta discharged from the human body, and has a storage space formed therein;
a coupling unit coupled to the main body;
a genital insertion unit connected to the coupling unit and having the second disposal space formed therein;
a male module, in which a second disposal space is formed therein and is configured to receive urine discharged from the human body, an opening unit; formed on one side of the second disposal space; configured to be opened to face the human body of the user; configured to have at least a part of male genitalia inserted therein; and provided in the main body, the male module further comprising a genitals fixing unit which is exposed to the second disposal space and which crimps and fixes the male module inserted into the second disposal space, the genitals fixing unit formed so as to be able to adjust the length exposed to the second disposal space, the genitals fixing unit the genitals fixing unit formed so as to be able to adjust the length exposed to the second disposal space, the genitals fixing unit comprising an adjustment member in which one side thereof is exposed to the second disposal space and the other side thereof is exposed to the outside of the male module so that the length exposed to the second disposal space can be adjusted in accordance with external manipulation;

a crimping member provided on one side of the adjustment member to crimp and fix the male genitalia; and a suction port: provided in the storage space: and configured to communicate with at least one of the first disposal space and the second disposal space to discharge excreta outside of the main body, wherein a through hole is formed in an insertion part of the genital insertion unit and has an internal thread formed around the adjustment member.

2. The excreta disposal device of claim 1, wherein at least a part of an inner surface of the male module is formed in the form of a downward inclined curve.

3. The excreta disposal device of claim 1, wherein at least a part of the male module is formed to be vertically rotatable.

4. The excreta disposal device of claim 1, wherein the genital insertion unit is connected to the coupling unit to be rotatable up and down.

5. The excreta disposal device of claim 1, wherein the genital insertion unit comprises:

a connecting unit connected to the coupling unit; and an insertion part which is provided in front of the connecting unit and has the opening unit formed therein.

6. The excreta disposal device of claim 5, wherein the insertion part is detachably formed in the connecting unit.

7. The excreta disposal device of claim 5, wherein the insertion part is linearly movable in the connecting unit and is formed to be able to adjust a length of the genital insertion unit.

8. The excreta disposal device of claim 7, wherein the device further comprises an extension unit formed to have a predetermined length; and provided: inside the connecting unit; and at a rear of the insertion part, and the connecting unit is provided with a fixing member configured to fix the extension unit.

9. The excreta disposal device of claim 7, wherein a plurality of catching grooves are formed at the rear end of the insertion part along the longitudinal direction of the insertion part, and the connecting unit is provided with a catching member selectively coupled to any one of the plurality of catching grooves.

10. The excreta disposal device of claim 7, wherein a screw thread is formed around the rear end of the insertion part, and the connecting unit is provided with a screw thread engaged with a screw thread of the insertion part, and a rotating member configured to move the insertion part back and forth in accordance with rotation.

11. The excreta disposal device of claim 1, wherein the coupling unit is detachably provided in the main body.

12. The excreta disposal device of claim 11, wherein the coupling unit projects to a predetermined length and is provided in the main body.

13. The excreta disposal device of claim 12, wherein the predetermined length is adjustable.

14. The excreta disposal device of claim 13, further comprising:

at least one or more coupling adjusting members which are provided so as to surround a portion of the coupling unit, and adjusts the depth of the coupling between the main body and the coupling unit by an increase and a decrease of a number of the coupling adjusting members.

15. The excreta disposal device of claim 1, wherein at least a part of the male module comprises a plurality of open regions in which a part of the periphery is opened so that the second disposal space is exposed to the outside, and a non-open region provided between the plurality of open regions.

16. The excreta disposal device of claim 15, further comprising:

a skin formed to cover the periphery of the male module to shield the open region.

* * * * *